(12) United States Patent
Richards et al.

(10) Patent No.: US 11,767,290 B2
(45) Date of Patent: Sep. 26, 2023

(54) METHOD FOR REMOVING $SO_3$ AND $CH_4$ FROM MIXTURES WHICH CONTAIN METHANE SULFONIC ACID

(71) Applicant: Veolia North America Regeneration Services, LLC, Houston, TX (US)

(72) Inventors: Alan K. Richards, Palm City, FL (US); John R. Jackson, Wilmington, NC (US)

(73) Assignee: Veolia North America Regeneration Services, LLC, Houston, TX (US)

( * ) Notice: Subject to any disclaimer, the term of this patent is extended or adjusted under 35 U.S.C. 154(b) by 0 days.

(21) Appl. No.: 17/714,310

(22) Filed: Apr. 6, 2022

(65) Prior Publication Data

US 2022/0332679 A1    Oct. 20, 2022

Related U.S. Application Data

(63) Continuation-in-part of application No. 17/224,566, filed on Apr. 7, 2021.

(51) Int. Cl.
| | | |
|---|---|---|
| *C07C 303/44* | (2006.01) | |
| *B01J 19/00* | (2006.01) | |
| *B01J 19/24* | (2006.01) | |
| *B01D 19/00* | (2006.01) | |
| *B01D 3/14* | (2006.01) | |

(52) U.S. Cl.
CPC ............ *C07C 303/44* (2013.01); *B01D 3/143* (2013.01); *B01D 19/0005* (2013.01); *B01D 19/0036* (2013.01); *B01D 19/0063* (2013.01); *B01D 19/0068* (2013.01); *B01J 19/0006* (2013.01); *B01J 19/2465* (2013.01); *B01J 2219/00051* (2013.01); *B01J 2219/00162* (2013.01)

(58) Field of Classification Search
None
See application file for complete search history.

(56) References Cited

U.S. PATENT DOCUMENTS

| | | |
|---|---|---|
| 2005/0070614 A1 | 3/2005 | Richards |
| 2020/0095197 A1 | 3/2020 | Richards |

FOREIGN PATENT DOCUMENTS

| | | |
|---|---|---|
| WO | WO 2018/208701 A1 | 11/2018 |
| WO | WO 2020/212299 A1 | 10/2020 |
| WO | WO 2021/023582 A1 | 2/2021 |

OTHER PUBLICATIONS

Chemical Reviews, Direct Capture of CO2 from Ambient Air, Ely S. Sanz-Perez, Christopher R. Murdock, Stephanie A. Didas, and Christopher W. Jones, 37 pages, Chem. Rev. 2016, 116, 11840-11876.

(Continued)

*Primary Examiner* — Amy C Bonaparte
(74) *Attorney, Agent, or Firm* — Dunlap Codding, P.C.

(57) ABSTRACT

A method for recovering a distillable, anhydrous methanesulfonic acid (MSA) liquid phase from an anhydrous 2-phase gas-liquid mixture wherein the anhydrous 2-phase gas-liquid mixture is generated by sulfonating methane ($CH_4$) with sulfur trioxide ($SO_3$) in an MSA-forming reactor, or reactor system, according to a radical chain reaction wherein the method comprises (i) separating the gas phase from the liquid phase, (ii) passing the separated liquid phase into a stripping column, and (iii) recovering the stripped anhydrous liquid phase.

10 Claims, 2 Drawing Sheets

(56) References Cited

OTHER PUBLICATIONS

Elsevier, Storage of carbon dioxide captured in a pilot-scale biogas upgrading plant by accelerated carbonation of industrial residues, Renato Baciocchi, Andrea Corti, Giulia Costa, Lidia Lombardi, Daniela Zingaretti, Energy Procedia 4 (2011) pp. 4985-4992; 8 pages.

International Search Report and Written Opinion (PCT/US2022/023592); dated Aug. 1, 2022; 10 pgs.

METHOD FOR REMOVING $SO_3$ AND $CH_4$ FROM MIXTURES WHICH CONTAIN METHANE SULFONIC ACID

CROSS REFERENCE TO RELATED APPLICATIONS

This application is a continuation in part of U.S. application Ser. No. 17/224,566 filed Apr. 7, 2021.

BACKGROUND OF THE INVENTION

The described and claimed inventive concept(s) relates to a method for removing sulfur trioxide ($SO_3$) and methane ($CH_4$) from a solution, i.e., a mixture, which contains methane-sulfonic acid (MSA), and, more particularly, to an improved method for recovering a distillable, anhydrous methane-sulfonic acid (MSA) liquid phase from an anhydrous 2-phase gas-liquid feed stream in which the liquid phase of the gas-liquid feed stream comprises a mixture of MSA, dissolved methane, $SO_3$, and, optionally, $H_2SO_4$, and the gas phase of the gas-liquid feed stream comprises unreacted methane and unreacted $SO_3$.

International Publication WO 2018/208701 A1 (Arkema, Inc.) describes a process for recovering MSA in a purified form from a composition which includes hydrocarbons, MSA, $SO_3$ and, optionally, sulfuric acid ($H_2SO_4$). The hydrocarbons are separated into a "light stream" while the MSA, $SO_3$ and $H_2SO_4$ are separated into a "heavy stream". The heavy stream is then contacted with a reactive additive, e.g., water, which results in the $SO_3$ being converted to $H_2SO_4$. The heavy stream is then passed to a distillation column to produce a distillate stream consisting essentially of MSA and a bottoms stream comprising $H_2SO_4$.

International Publication WO 2020/212299 A1 (BASF SE) describes a process for producing anhydrous MSA from $CH_4$ and $SO_3$ which includes a reaction set-up that begins by generating a first MSA stream which includes unreacted $SO_3$ and unreacted $CH_4$ under pressure. A reactive agent is added to, i.e., mixed with, the first MSA stream under conditions effective to cause reaction of the $SO_3$ with the reactive agent to produce a heavy reaction product having a boiling point higher than the boiling point of MSA. Hydrocarbons are separated from the first MSA stream, and then the first MSA stream, including the heavy reaction product, is distilled whereby a distillate stream comprising MSA is separated from the heavy reaction product. In one embodiment the reactive agent is water, and the heavy reaction product is $H_2SO_4$.

Methane-sulfonic acid (MSA) is commercially produced according to a process which integrates sulfonation chemistry and selective extraction under anhydrous conditions, to combine methane ($CH_4$) and sulfur trioxide ($SO_3$) in a manner which converts them into MSA having a purity which can be greater than 90 percent. The steps of the process include sulfonating methane ($CH_4$) with sulfur trioxide ($SO_3$) in an MSA-forming reactor, or reactor system, according to a radical chain reaction, which forms a 2-phase gas-liquid mixture. This mixture, which includes MSA in an acidic media, and may also contain sulfuric acid ($H_2SO_4$), is sometimes referred to as a rich acid mixture. This rich acid mixture contains an enriched concentration of MSA compared to $H_2SO_4$, but it may also contain substantial quantities of $CH_4$ and $SO_3$. The MSA must be separated from the $CH_4$, $SO_3$ and $H_2SO_4$ to yield an MSA finished product for commercial applications that is low in sulfate. The need exists, therefore, to develop an improved method for recovering a distillable, anhydrous methane-sulfonic acid (MSA) as a liquid phase from the 2-phase gas-liquid mixture without having to introduce an independent reactive agent, such as water, into the liquid phase to react with the $SO_3$.

SUMMARY OF THE INVENTION

The described and claimed inventive concept(s) relates to a method for recovering a distillable, anhydrous methane-sulfonic acid (MSA) liquid phase from an anhydrous 2-phase gas-liquid mixture which is generated by sulfonating methane ($CH_4$) with sulfur trioxide ($SO_3$) in an MSA-forming reactor, or reactor system, according to a radical chain reaction. The liquid phase of the gas-liquid feed stream which exits the MSA-forming reactor comprises a mixture of MSA, dissolved methane, $SO_3$, and optionally $H_2SO_4$. The gas phase of the gas-liquid feed stream comprises unreacted methane and unreacted $SO_3$. The initial pressure of the 2-phase gas-liquid feed stream is typically in the range of from 100 psi up to 2000 psi, and the temperature of the two-phase gas-liquid feed stream is in the range of from 40° C. up to 90° C.

The method comprises separating the liquid phase from the gas phase of the 2-phase gas-liquid mixture while simultaneously reducing the pressure of the separated liquid and gas phases to a value which is at least 2 to 10 psi below the initial pressure of the 2-phase gas-liquid mixture. According to one embodiment, the pressure of the separated liquid and gas phases is reduced to a value in the range of from 5 psi to 2 psi below the initial pressure of the 2-phase gas-liquid mixture.

The separated gas phase, comprising primarily unreacted $CH_4$, can be returned to the MSA-forming reactor. The separated liquid phase becomes a feed stream that is passed to a stripping column while a stripping gas is simultaneously introduced into the stripping column in countercurrent flow to the liquid phase feed stream.

The flow rate of stripping gas into the stripping column is typically in the range of from 3 to 10 moles of stripping gas per liter of $SO_3$ in the separated liquid phase feed stream, although a higher or lower flow rate of stripping gas can also be used with satisfactory results. The temperature of the stripping column is maintained in a range of from ambient up to about 160° C., and the pressure of the stripping column can be above or below ambient, i.e., atmospheric, pressure, although best results have been shown to occur in simulation examples when the stripping column is operated at ambient pressure with a desired number of stages, such as, for example, from at least 3 up to 15 stages. According to an alternate embodiment, the temperature of the stripping column is maintained in a range of from ambient up to about 130° C.

The $SO_3$ concentration in the separated liquid phase, i.e., the feed stream, which exits the stripping column can be reduced to a value in the range of from about 5 ppm to 1000 ppm without the addition of water or any other reactive agent. According to an alternate embodiment, the $SO_3$ concentration in the separated liquid phase exiting the stripping column is in the range of from 5 ppm to 50 ppm. The separated liquid phase, which has been maintained as an anhydrous mixture, can then be passed to at least one distillation column wherein the temperature can be maintained in an operable range that avoids decomposition of the MSA.

According to one embodiment, the stripping gas is selected from the group consisting essentially of an inert gas, nitrogen, methane, natural gas and mixtures thereof. Inert gases useful in practicing the inventive concept(s) described and claimed herein include helium and argon. Air can also be employed as a stripping gas if the quantity is sufficiently large to maintain any methane gas or other hydrocarbon gases exiting the stripper column below a concentration that could support combustion. According to an alternate embodiment, the preferred stripping gas is selected from methane, natural gas and mixtures thereof because of their commercial availability and their relevance to the preferred radical chain reaction that is followed to form MSA.

DETAILED DESCRIPTION OF THE INVENTION

Figure 1:
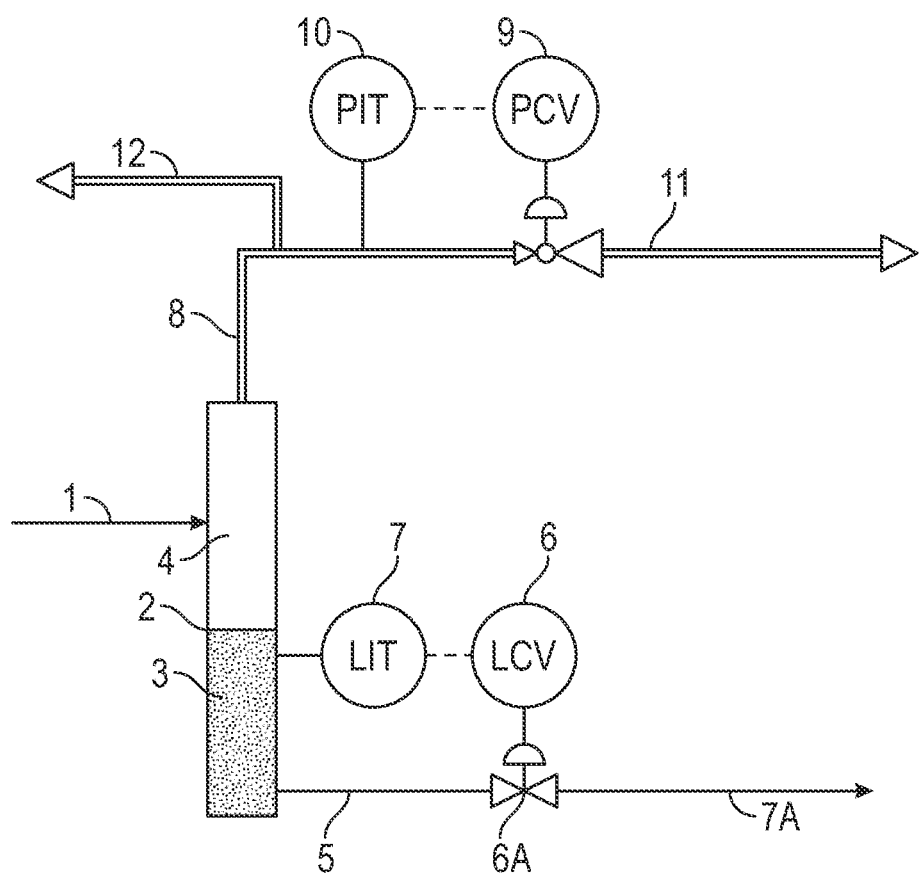
FIG. 1 is a simplified schematic drawing of a separation vessel which functions to separate the liquid phase from the gas phase of the 2-phase gas-liquid mixture according to the described and claimed inventive concept(s).

Before explaining at least one embodiment of the presently disclosed and claimed inventive concept(s) in detail, it is to be understood that the presently disclosed and claimed inventive concept(s) is not limited in its application to the details of construction and the arrangement of the components or steps or methodologies set forth in the following description or illustrated in the drawings. The presently disclosed and claimed inventive concept(s) is capable of other embodiments or of being practiced or carried out in various ways. Also, it is to be understood that the phraseology and terminology employed herein is for the purpose of description and should not be regarded as limiting.

Unless otherwise defined herein, technical terms used in connection with the presently disclosed and claimed inventive concept(s) shall have the meanings that are commonly understood by those of ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which this presently disclosed and claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles and/or methods disclosed and claimed herein can be made and executed without undue experimentation in light of the present disclosure. While the articles and methods of the presently disclosed and claimed inventive concept(s) have been described in terms of particular embodiments, it will be apparent to those of skill in the art that variations may be applied to the articles and/or methods and in the steps or in the sequence of steps of the method described herein without departing from the concept, spirit and scope of the presently disclosed and claimed inventive concept(s). All such similar substitutes and modifications apparent to those skilled in the art are deemed to be within the spirit, scope and concept of the presently disclosed and claimed inventive concept(s) as defined by the appended claims.

As utilized in accordance with the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example, but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent. The use of the term "at least one" will be understood to include one as well as any quantity more than one, including but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first," "second," "third," "fourth," etc.) is solely for the purpose of differentiating between two or more items and is not meant to imply any sequence or order or importance to one item over another or any order of addition, for example.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

The inventive concept(s) will now be explained according to one embodiment in relation to an anhydrous 2-phase gas-liquid mixture of the type which is generated in commercial processes for producing MSA by sulfonating methane ($CH_4$) with sulfur trioxide ($SO_3$) in an MSA-forming reactor, or reactor system, according to a radical chain reaction. Such a radical chain reaction is described, for example, in U.S. Pat. No. 7,282,603 and in U.S. Patent Publication No. 2020/0002276 A1, the teachings of which are incorporated herein in their entirety by reference. The instant inventive concept(s) focuses on a method for recovering a distillable, anhydrous methane-sulfonic acid (MSA) liquid phase from the anhydrous 2-phase gas-liquid mixture without having to introduce an independent reactive agent, such as water, into the mixture to react with any $SO_3$ that may also be present.

The method comprises separating the liquid phase from the gas phase of the 2-phase gas-liquid mixture and then reducing the pressure of the separated liquid and gas phases to a value which is at least 2 psi up to 10 psi below the initial pressure of the 2-phase gas-liquid mixture. Downstream pressure reduction is accomplished in a way that will maintain an appropriate operating pressure in the MSA forming reactor(s), or reactor system, and the discharge flowrate of the separated liquid phase is controlled to correspond to the flow rate of the feed streams into the MSA forming reactor(s). According to one embodiment, with reference to FIG. 1, the two-phase gas-liquid mixture which exits the MSA reactor(s) is passed, or is introduced, to separation vessel 2 via line 1. Liquid passes to the lower portion 3 of the separation vessel while gas passes to the upper portion 4 of the separation vessel. Separation vessel 2 functions as a surge tank wherein the fluid velocities in the lower portion 3 and gas velocities in the upper portion 4 are low enough to drive effective gas-liquid separation. The volume of liquid in the lower portion 3 of separation vessel 2 is maintained relatively constant by level control valve 6 and transmitter 7. Flow rate of the liquid portion which ultimately exits separation vessel 2 via lines 5 and 7A is controlled by pressure control, i.e., pressure let-down, valve 6A. While the pressure in line 7A can be any pressure from ambient to as high as the operating pressure of the MSA reactor(s), optimum operability is achieved when the pressure in line 7A is reduced to a value which can drive the exiting liquid phase to the next unit operation, e.g., to a value in the range of from 2 psi to 10 psi above the pressure of the next unit operation.

Figure 2:
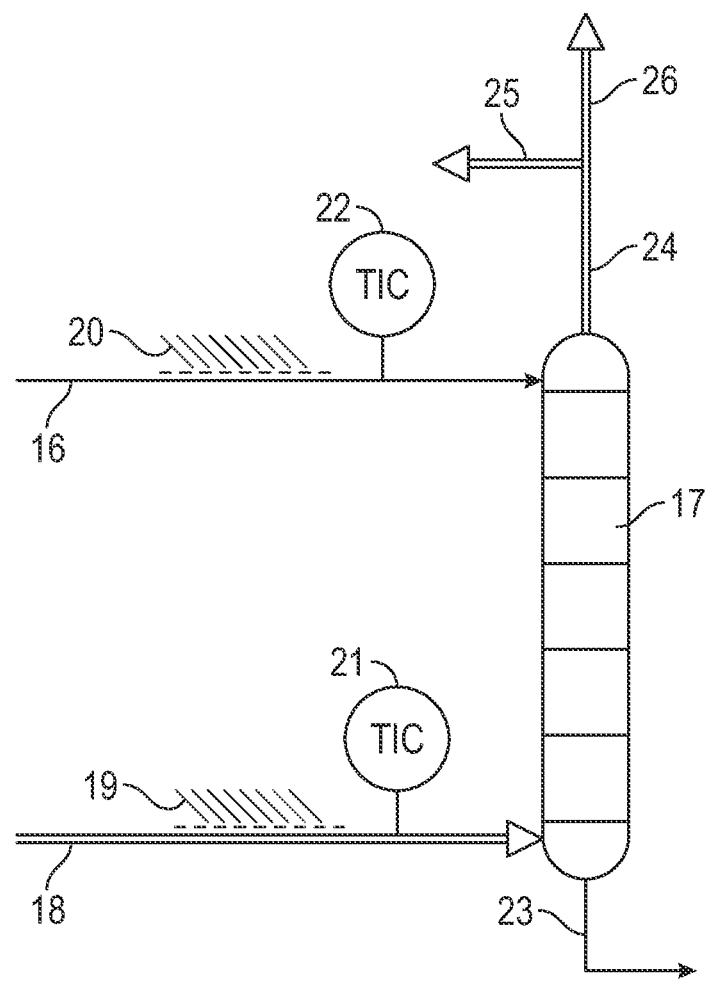
FIG. 2 is a simplified schematic drawing of a stripping column for use according to the described and claimed inventive concept(s).

A portion of the separated gas phase which exits separation vessel 2 via line 8, comprising primarily unreacted $CH_4$, can be returned, i.e., recycled, to the MSA-forming reactor via line 12. The balance of the separated gas phase, which exits separation vessel 2 via line 8, becomes a feed stream 11 that is passed to the bottom of a stripping column via line 18 as shown in FIG. 2. Pressure of the exiting gas phase in line 8 is controlled with pressure transmitter (PIT) 10 in communication with pressure control valve (PCV) 9. Additional stripping gas is simultaneously introduced into the stripping column via line 18 in countercurrent flow to the liquid phase feed stream that enters column 17 via line 16. Stripping gas exits stripping column 17 via lines 24, 25 and 26 as shown. A distillable, anhydrous methane-sulfonic acid (MSA) liquid phase is recovered from the stripping column via line 23. Being anhydrous, the liquid phase contains no water that could operate to raise the boiling point of the MSA in the liquid phase to undesirably high levels.

FIG. 2 is a simplified schematic drawing of a stripping column 17 for use according to the described and claimed inventive concept(s). The separated liquid phase, which is recovered from separation vessel 2 via line 7A and comprises a mixture of MSA, dissolved methane, and $SO_3$, but may also contain an amount of $H_2SO_4$, is fed to stripping column 17 via line 16. Stripping gas enters the bottom of stripping column 17 via line 18, as shown, to flow countercurrent to the flow of the separated liquid phase that enters stripping column 17 via line 16.

Stripping column 17 can have multiple theoretical stages that are positioned within the column to lower the initial $SO_3$ concentration in the separated liquid phase to a value which can be in the range of 500 ppm. With a predetermined number of theoretical stages in stripping column 17, for example in the range of from at least 3 up to 15 stages, the final $SO_3$ concentration in the separated liquid phase which exits stripping column 17 via line 23 can be as low as 10 ppm or even lower, e.g., 5 ppm.

As noted above, stripping gas enters the bottom of stripping column 17 via line 18 and flows countercurrent with respect to the separated liquid phase, which enters the top of the column via line 16. The flow rate of stripping gas into stripping column 17 is typically in the range of from 3 to 10 moles of stripping gas per liter of $SO_3$ in the separated liquid phase feed stream, although a higher or lower flow rate of stripping gas can also be used with satisfactory results. According to an alternate embodiment, the stripping gas is selected from the group consisting essentially of an inert gas, nitrogen, methane, natural gas and mixtures thereof. Inert gases useful in practicing the inventive concept(s) described and claimed herein include, but are not limited to, helium and argon. According to an alternate embodiment, the preferred stripping gases are selected from methane and natural gas because of their commercial availability and their relevance to the preferred radical chain reaction that is followed to form MSA.

The temperature of stripping column 17 can be maintained in a range of from ambient up to about 160° C., although best results are believed to be achieved when the temperature of stripping column 17 is maintained at a value in the range of from 100° C. to 130° C. A consistent temperature range can be achieved by deploying heaters 19 and 20 in conjunction with temperature controller/thermostats 21 and 22 as shown in FIG. 2 in relation to feed lines 16 and 18.

The pressure of stripping column 17 can be above or below ambient, i.e., atmospheric, pressure, although the most practical configuration is achieved by operating the stripping column at ambient pressure with the desired number of stages. An effective number of stages in stripping column 17 to achieve best results, for example, would be from 3 to 15 stages. Selecting an effective number of stages in stripping column 17 to accommodate a specific set of operating conditions is well within the capabilities of one skilled in chemical engineering and chemical operations. Operating stripping column 17 under vacuum may improve stripping efficiency, but such an arrangement can add equipment, complexity and additional capital and operating expense to the system.

The $SO_3$ concentration in the separated liquid phase, i.e., the liquid stream, which exits stripping column 17 via line 23 according to the described inventive concept(s) will have a value in the range of from about 5 ppm to 1000 ppm, and this is achieved without the addition of water or any other reactive agent, meaning the liquid phase remains anhydrous and in condition to be fed to one or more distillation units for final processing and recovery of high purity MSA. According to one embodiment, the $SO_3$ concentration in the separated liquid phase exiting stripping column 17 is in the range of from 5 ppm to 50 ppm.

Example 1: A stripping column to remove $SO_3$ from a mixture of the type generated in an MSA-forming reactor comprising MSA, $H_2SO_4$, and $SO_3$ according to the described and claimed inventive concept(s) was developed, and its operation was simulated using ChemCAD chemical process simulation software. Design and operating conditions were selected for several scenarios to demonstrate that $SO_3$ can successfully be removed from the MSA liquid mixture (i.e., the separated liquid phase referred to above which exits separation vessel 2) using a stripping column and thereby achieve a distillable anhydrous MSA liquid phase without the addition of water or any other reactive agent. In all cases, gas flow through the stripping column was countercurrent to the incoming $MSA/SO_3$ containing liquid mixture fed to the top of the column, with stripping gas being fed to the bottom of the column. In all cases, the simulated stripping column was designed with at least three or more theoretical stages, and in all cases, the concentration of $SO_3$ in the resulting MSA liquid phase leaving the column was below 100 ppm. Having a small amount of $SO_3$ in the resulting distillable anhydrous MSA liquid phase, for example, not more than from about 5 to 1000 ppm, is not believed to affect MSA recovery.

Also noteworthy was the observation that the MSA concentration in the initial mixture comprising MSA, $H_2SO_4$, and $SO_3$ did not appear to be a factor in stripping column performance. Tabulated data used in the simulation can be seen in Table 1.

and sulfuric acid or MSA under the stripper conditions in the simulations. The term "adduct" is used herein to mean a product of a direct addition of two or more distinct molecules, resulting in a single reaction product that contains all atoms of all the components. The resultant reaction product, i.e., the adduct, is considered a distinct molecular species.

An adduct would put a lower limit on the concentration to which $SO_3$ could be removed in a stripper depending upon the operating conditions and reversibility of the adduct reaction. An adduct of, for example, 1 wt %, may interfere with the operation and performance of a downstream distillation system if the adduct reaction is reversed.

In the following example, i.e., Example 2, a laboratory apparatus was set up to determine if an adduct exists that could later form $SO_3$ at a concentration that could render the stripped solutions unsuitable as feedstock to a distillation column that recovers MSA as a high-quality product. The following test was conducted in a simple flask rather than an engineered stripping column. One skilled in the art would understand that a properly designed stripping column could be much more efficient at removing $SO_3$ than a flask, and, therefore, successful removal of $SO_3$ in a flask would confirm the findings from the ChemCAD simulation described in the Example.

Example 2: A 500 ml Erlenmeyer flask with a stirring bar heated on a hotplate stirrer was used as the stripping flask. The stripping flask was connected to two absorbing cylinders connected in series. The absorbing cylinders were filled with a suitable $SO_3$ absorbing media, such as, for example, water or a caustic solution. Dry air was fed through a drying agent to the bottom of the stripping flask through a fine tipped glass tube, then from the top of the stripping flask to the bottom of a first absorber, and then from the top of the first absorber to the bottom of a second absorber. Fine tipped glass tubes were used to introduce the gas into both absorbers. The second absorber was open to atmosphere in a fume

TABLE 1

| Liquid composition, | | | | | | | | |
|---|---|---|---|---|---|---|---|---|
| MSA | 35.3% | 35.3% | 35.3% | 35.3% | 35.3% | 87.0% | 87.0% | 87.0% |
| H2SO4 | 55.5% | 55.5% | 55.5% | 55.5% | 55.5% | 3.8% | 3.8% | 3.8% |
| SO3 | 9.2% | 9.2% | 9.2% | 9.2% | 9.2% | 9.2% | 9.2% | 9.2% |
| Temperature, °C. | 130 | 130 | 130 | 130 | 130 | 130 | 130 | 130 |
| Moles of stripping gas per liter of liquid | 2.44 | 3.07 | 4.18 | 6.36 | 16.16 | 2.83 | 3.54 | 4.80 |
| Number of theor stages | 15 | 10 | 7 | 5 | 3 | 15 | 10 | 7 |

| | Liquid composition, | | | | | | |
|---|---|---|---|---|---|---|---|
| | MSA | 87.0% | 87.0% | 31.1% | 35.3% | 35.3% | 35.3% | 35.3% |
| | H2SO4 | 3.8% | 3.8% | 48.9% | 55.5% | 55.5% | 55.5% | 55.5% |
| | SO3 | 9.2% | 9.2% | 20.0% | 9.2% | 9.2% | 9.2% | 9.2% |
| | Temperature, °C. | 130 | 130 | 130 | 100 | 115 | 130 | 150 |
| | Moles of stripping gas per liter of liquid | 7.17 | 16.45 | 6.52 | 20.21 | 10.98 | 6.36 | 2.92 |
| | Number of theor stages | 5 | 3 | 5 | 5 | 5 | 5 | 5 |

The foregoing Example 1, using ChemCAD chemical process simulation software, demonstrates that $SO_3$ can be removed from the as mentioned solutions to less than 2000 ppm in a properly designed stripper. However, the Example is based on the premise that there is no adduct between $SO_3$ hood. Temperature of the stripping solution in the flask was measured with a thermocouple and controlled by the hot plate. The pressure in the stripping flask was the sum of ambient pressure plus the liquid head pressure in the two absorbers. This resulted in a back-pressure of about 1 psig in the stripping flask.

A solution comprising 58.8% $H_2SO_4$, 38.3% MSA, 2.9% $SO_3$ was prepared and stored in an appropriate container. 699 grams (about 410 ml) of the solution was weighed into the Erlenmeyer stripping flask. The flask was immediately connected to the absorbers and sealed from atmospheric air. A stream of dry air was immediately started at a flowrate of 1.7 liters per minute and temperature was then elevated to 150° C. The apparatus was run under these conditions for 14.2 hours at which point the test was stopped. Findings were as follows:

There was no visible presence of free $SO_3$ when the hot stripping flask was unsealed and exposed to air. Even small levels of $SO_3$ in a solution, particularly hot solutions, produce a very noticeable white vapor just above the solution surface. The white vapor is sulfur trioxide combining with water vapor in the air to produce very small droplets of sulfuric acid, which look like white smoke to the naked eye. No free $SO_3$ was observed in the solution. However, the absence of free $SO_3$ does not prove there was no adduct in the solution.

The stripper solution was then analyzed for $SO_3$. The analytical procedure used was capable of identifying both free $SO_3$ and $SO_3$ in an $SO_3$/MSA adduct. The analysis showed no $SO_3$ was present in the solution down the detection limit of the analytical procedure of 2000 ppm $SO_3$. According to Example 2 a properly designed stripper will work to remove $SO_3$ down to 2000 ppm or less in a sulfuric acid MSA solution.

As those skilled in the art will appreciate, numerous modifications and variations of the described and claimed inventive concept(s) are possible in light of these teachings, and all such modifications and variations are contemplated hereby. The present invention contemplates and claims those inventions that may result from the combination of features described herein and those of the cited prior art references which complement the features of the present invention.

What is claimed is:

1. A method for recovering a distillable, anhydrous methane-sulfonic acid (MSA) liquid phase from an anhydrous 2-phase gas-liquid feed stream, said 2-phase gas-liquid feed stream having an initial pressure in a range of from 100 psi up to 2000 psi, and a temperature in the range of from 40° C. up to 90° C. wherein:
   (i) the liquid phase of the gas-liquid feed stream comprises a mixture of MSA, dissolved methane, $SO_3$, and, optionally, $H_2SO_4$, and
   (ii) the gas phase of the gas-liquid feed stream comprises methane and $SO_3$, said method comprising:
   (A) separating the gas phase from the liquid phase by reducing the pressure of the gas and liquid phases to a value which is at least 2 up to 10 psi below the initial pressure in the 2-phase gas-liquid feed stream;
   (B) passing the separated liquid phase into a stripping column while simultaneously passing a stripping gas into the stripping column in countercurrent flow to the separated liquid phase, wherein the flow rate of stripping gas is in the range of from 3 to 10 moles of stripping gas per liter of $SO_3$ in the separated liquid phase, and the temperature of the stripping column is in the range of from ambient up to 160° C., with the result that the $SO_3$ concentration in the separated liquid phase which exits the stripping column has been reduced to a value in the range of from 5 ppm to 1000 ppm without the addition of water or any other reactive agent.

2. The method of claim 1, wherein the temperature of the stripping column is in the range of from ambient up to 130° C.

3. The method of claim 1, wherein the temperature of the stripping column is in the range of from 100° C. up to 130° C.

4. The method of claim 1, or claim 2, wherein the stripping gas is selected from the group consisting of an inert gas, nitrogen, methane, natural gas and mixtures thereof.

5. The method of claim 1, or claim 2, which includes the additional step of passing the separated liquid phase which exits the stripping column to at least one distillation column.

6. The method of claim 4, wherein the stripping gas which exits the stripping column is blended with fresh methane ($CH_4$) and recycled to an MSA-forming reactor or an MSA-forming reactor system.

7. The method of claim 1, wherein the concentration of $SO_3$ in the gas phase of the gas-liquid feed stream is in the range of from 2 to 50 wt %.

8. The method of claim 1, wherein the gas phase separated in step (A) is recycled to an MSA-forming reactor or an MSA-forming reactor system.

9. The method of claim 1, wherein the 2-phase gas-liquid mixture is passed, or is introduced, to a separation vessel having a lower portion and an upper portion wherein liquid passes to the lower portion while gas passes to the upper portion wherein fluid velocity in the lower portion and gas velocity in the upper portion are low enough to drive gas-liquid separation.

10. The method of claim 9, wherein the volume of liquid in the lower portion of the separation vessel is maintained relatively constant by a level control valve, and the flow rate of the liquid portion which exits the separation vessel is controlled by a pressure control valve.

* * * * *